(12) United States Patent
Koga et al.

(10) Patent No.: US 9,518,004 B2
(45) Date of Patent: Dec. 13, 2016

(54) REDUCED COENZYME $Q_{10}$ DERIVATIVE AND METHOD FOR PRODUCTION THEREOF

(71) Applicant: KANEKA CORPORATION, Osaka-shi (JP)

(72) Inventors: Teruyoshi Koga, Takasago (JP); Yoshihisa Okamoto, Takasago (JP); Takao Yamaguchi, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/649,369

(22) PCT Filed: Dec. 2, 2013

(86) PCT No.: PCT/JP2013/082375
§ 371 (c)(1),
(2) Date: Jun. 3, 2015

(87) PCT Pub. No.: WO2014/087972
PCT Pub. Date: Jun. 12, 2014

(65) Prior Publication Data
US 2015/0307440 A1    Oct. 29, 2015

(30) Foreign Application Priority Data

Dec. 3, 2012  (JP) ................. 2012-264558

(51) Int. Cl.
*C07C 68/00*  (2006.01)
*C07C 68/08*  (2006.01)
*C07C 69/96*  (2006.01)

(52) U.S. Cl.
CPC ............. *C07C 69/96* (2013.01); *C07C 68/00* (2013.01); *C07C 68/08* (2013.01); *C07C 2101/08* (2013.01)

(58) Field of Classification Search
CPC ................. C07C 68/00; C07C 68/08
See application file for complete search history.

(56) References Cited

U.S. PATENT DOCUMENTS

| | | | | |
|---|---|---|---|---|
| 4,432,987 A * | 2/1984 | Barth | ............ | C07D 499/00 514/193 |
| 5,721,359 A * | 2/1998 | Dunn | ............ | C07D 501/00 540/225 |
| 6,127,417 A | 10/2000 | Guarnieri et al. | | |
| 7,145,002 B2 * | 12/2006 | Brands | ............ | C07D 477/20 540/350 |
| 2011/0144376 A1 | 6/2011 | Takata et al. | | |

FOREIGN PATENT DOCUMENTS

| | | | |
|---|---|---|---|
| JP | 56-123927 A | 9/1981 | |
| JP | 62-31700 B2 | 7/1987 | |
| JP | 10-509732 A | 9/1998 | |
| JP | 2003-104945 A | 4/2003 | |
| JP | 2005-211020 A | 8/2005 | |
| JP | 2008-231077 A | 10/2008 | |
| WO | WO 96/17626 | * | 6/1996 |
| WO | WO 98/04512 A1 | | 2/1998 |
| WO | WO 2007/095630 A2 | | 8/2007 |
| WO | WO 2007/095631 | * | 8/2007 |
| WO | WO 2010/021034 A1 | | 2/2010 |

OTHER PUBLICATIONS

Morissette et al. (Advanced Drug Delivery Reviews, 56, (2004) p. 275-300.*
Vogel, A.I.(Vogel, Arghur I.; Practical Organic Chemistry, Longman Group Limited London, 1956, 3rd.*
Stowell (J. Am. Chem. Soc. 1998, 120, 1657-1664).*
International Search Report issued Feb. 25, 2014, in PCT/JP2013/082375, filed Dec. 2, 2013.
Mikael Turunen, et al., "Blood Concentration of Coenzyme $Q_{10}$ Increases in Rats When Esterified Forms Are Administered", Biochemical and Molecular Action of Nutrients, The Journal of Nutrition, vol. 129, No. 12, 1999, pp. 2113-2118.
Theodora W. Greene, et al., "Protective Groups in Organic Synthesis", John Wiley & Sons, Inc., Second Edition, 1998, pp. 165-167.

* cited by examiner

*Primary Examiner* — Valerie Rodriguez-Garcia
(74) *Attorney, Agent, or Firm* — Oblon, McClelland, Maier & Neustadt, L.L.P.

(57) ABSTRACT

A reduced coenzyme $Q_{10}$ derivative represented by formula (1),

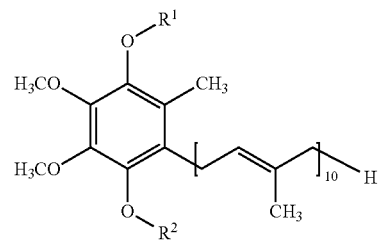

wherein $R^1$ and $R^2$ are each independently H or an alkoxycarbonyl group represented by formula (2),

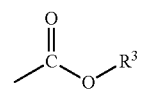

and at least one of them is an alkoxycarbonyl group represented by the formula (2); in the formula (2), $R^3$ is an optionally substituted linear, branched, or cyclic alkyl group having 1 to 20 carbon atoms, an optionally substituted aryl group having 6 to 20 carbon atoms, or an optionally substituted heteroaryl group having 4 to 20 carbon atoms, and when $R^3$ is a group substituted with polyethylene glycol, the molecular weight of the polyethylene glycol is not more than 300.

20 Claims, No Drawings

REDUCED COENZYME Q₁₀ DERIVATIVE AND METHOD FOR PRODUCTION THEREOF

TECHNICAL FIELD

The present invention relates to a novel reduced coenzyme $Q_{10}$ derivative that can be used for foods and drinks such as health foods or foods with health claims (foods for specified health use (FOSHU) and foods with nutrient function claims), pharmaceutical products, quasi drugs, cosmetics, and so on and that is stable against molecular oxygen and superior in oral absorbability and also relates to a method for the production thereof.

BACKGROUND ART

Reduced coenzyme $Q_{10}$ is a compound that not only exhibits higher oral absorbability as compared with oxidized coenzyme $Q_{10}$ but also is very useful as an antioxidant, and it can be produced by reducing oxidized coenzyme $Q_{10}$ obtained by a conventional method such as synthesis, fermentation, and extraction from a natural product. However, reduced coenzyme $Q_{10}$ is prone to oxidation into oxidized coenzyme $Q_{10}$ by molecular oxygen, and therefore a remaining important challenge is to maintain reduced coenzyme $Q_{10}$ with stability during processing of reduced coenzyme $Q_{10}$ into a base material or a composition for food, food with nutrient function claims, food for specified health use, nutritional supplement, nutritional product, animal drug, drink, feed, cosmetic, pharmaceutical product, therapeutic drug, prophylactic drug, etc. and/or during storage after the processing.

Various methods aiming improvement in stability or improvement in absorbability of reduced coenzyme $Q_{10}$ have heretofore been studied.

For example, there is known a method of improving oxidation stability by protecting a hydroxyl group of reduced coenzyme $Q_{10}$ with an acyl group or an ether group (Patent Document 1).

On the other hand, as to a method for improving absorbability, improvement in hydrophilicity has heretofore been believed to lead to improvement in absorbability because reduced coenzyme $Q_{10}$ is higher in absorbability than oxidized coenzyme $Q_{10}$, and there have been reported derivatives with a hydrophilic group such as PEG (polyethylene glycol) having been introduced (Patent Document 2), derivatives with glycine having been introduced (Patent Document 3), and derivatives with succinic acid having been introduced (NON-Patent Document 1).

PRIOR ART DOCUMENTS

Patent Documents

Patent Document 1: WO 98/04512
Patent Document 2: JP-T-10-509732
Patent Document 3: JP-A-2003-104945

Non-Patent Document

Non-Patent Document 1: Journal of Nutrition (1999), 129(12), 2113-2118

DISCLOSURE OF THE INVENTION

Problems to be Solved by the Invention

In view of the above, an object of the present invention is to provide a novel reduced coenzyme $Q_{10}$ derivative that is high in stability against oxidation, superior in oral absorbability, and easy to apply to food, health food, food with nutrient function claims, food for specified health use, supplement, nutritional supplement, nutritional product, animal drug, drink, feed, pet food, cosmetic, pharmaceutical product, therapeutic drug, prophylactic drug, and so on.

Solutions to the Problems

As a result of earnest studies, the present inventors have accomplished the present invention by finding that a reduced coenzyme $Q_{10}$ derivative having a specific alkoxycarbonyl group introduced to it is surprisingly not only stable against oxidation but also superior in oral absorbability even though water solubility is lowered by the introduction of the substituent.

That is, the present invention relates to a novel reduced coenzyme $Q_{10}$ derivative represented by the following formula (1):

[Chemical Formula 1]

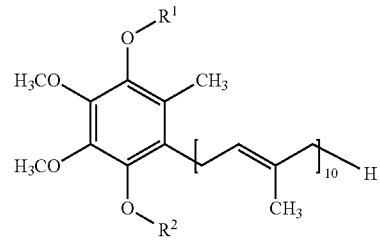

(1)

wherein $R^1$ and $R^2$ are each independently H or an alkoxycarbonyl group represented by formula (2):

[Chemical Formula 2]

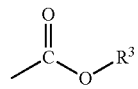

(2)

and at least one of them is an alkoxycarbonyl group represented by the formula (2); in the formula (2), $R^3$ is an optionally substituted linear, branched, or cyclic alkyl group having 1 to 20 carbon atoms, an optionally substituted aryl group having 6 to 20 carbon atoms, or an optionally substituted heteroaryl group having 4 to 20 carbon atoms, and when $R^3$ is a group substituted with polyethylene glycol, the molecular weight of the polyethylene glycol is not more than 300.

Moreover, the present invention also relates to a crystal of a novel reduced coenzyme $Q_{10}$ derivative represented by the above formula (1).

Furthermore, the present invention also relates to a method for producing a reduced coenzyme $Q_{10}$ derivative represented by the above formula (1) characterized by reacting reduced coenzyme $Q_{10}$ with an alkoxycarbonylation agent in the presence of a base.

Effects of the Invention

According to the present invention, a novel reduced coenzyme $Q_{10}$ derivative that can be used for drugs, health foods, etc. and that is superior in absorbability and oxygen stability can be provided as a prodrug of oxidized coenzyme $Q_{10}$ or an equivalent to a stabilized reduced coenzyme $Q_{10}$.

MODE FOR CARRYING OUT THE INVENTION

The present invention is described in detail below.

The reduced coenzyme $Q_{10}$ derivative of the present invention is a novel compound represented by the following formula (1):

[Chemical Formula 3]

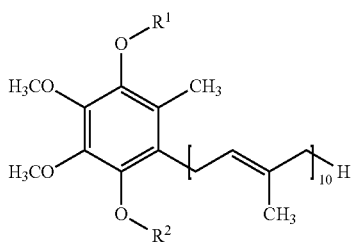

(1)

(hereinafter sometimes referred to as compound (1)).

Here, $R^1$ and $R^2$ of the compound (1) are each independently H or an alkoxycarbonyl group represented by the following formula (2):

[Chemical Formula 4]

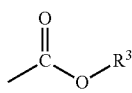

(2)

It is noted that at least one of $R^1$ and $R^2$ is an alkoxycarbonyl group represented by the formula (2). Characteristically, $R^3$ is A) an optionally substituted linear, branched or cyclic alkyl group having 1 to 20 carbon atoms, B) an optionally substituted aryl group having 6 to 20 carbon atoms, or C) an optionally substituted heteroaryl group having 4 to 20 carbon atoms. It is noted that when $R^3$ is a substituted group and the substituent is polyethylene glycol, the molecular weight of the polyethylene glycol is limited to not more than 300.

A) Alkyl Group

Examples of the substituent that may bonds to the alkyl group include a halogen group (preferably, a chloro group, a bromo group, especially, a chloro group), a nitro group, a nitrile group, an alkoxy group (preferably, a $C_{1-4}$ alkoxy group, such as a methoxy group and an ethoxy group), an alkenyl group (preferably, a vinyl group, a propenyl group, etc.), an alkynyl group, and an aryl group (a phenyl group, a naphthyl group, etc.).

The optionally substituted, linear, branched, or cyclic alkyl group having 1 to 20 carbon atoms is not particularly limited and examples thereof include a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, a sec-pentyl group, a neopentyl group, a 2-methylbutyl group, a 3-methylbutyl group, a cyclopentyl group, a n-hexyl group, a 2-methylpentyl group, a 2,2-dimethylbutyl group, a 2,3-dimethylbutyl group, a methylcyclopentyl group, a cyclohexyl group, a n-heptyl group, a 2-methylhexyl group, a 3-methylhexyl group, a 2,3-dimethylpentyl group, a 2,4-dimethylpentyl group, a methylcyclohexyl group, a n-octyl group, a 2,2,3-trimethylpentyl group, an isooctyl group, an ethylcyclohexyl group, a n-nonyl group, a 2,2,5-trimethylhexyl group, a n-decanyl group, a n-undecanyl group, a n-dodecanyl group, a 2-chloroethyl group, a 2-cyanohexyl group, a 2-methoxyhexyl group, a 2-nitrohexyl group, an allyl group, a crotyl group, a benzyl group, a 4-nitrobenzyl group, a 4-methoxybenzyl group, and a 4-chlorobenzyl group.

The number of the carbon atoms of the alkyl group is preferably from 1 to 15, more preferably from 2 to 10, and particularly preferably from 3 to 8. When the number of the carbon atoms of the alkyl group is not less than 3, the alkyl group is preferably branched or cyclic. Preferably, no substituent is bonded to the alkyl group.

B) Aryl Group, C) Heteroaryl Group

Examples of the substituent that may be bonded to the aryl group or the heteroaryl group include a halogen group (preferably, a chloro group and a bromo group, especially, a chloro group), a nitro group, a nitrile group, an alkoxy group (preferably, a $C_{1-4}$ alkoxy group such as a methoxy group and an ethoxy group), and an alkyl group (preferably, a $C_{1-4}$ alkyl group such as a methyl group and an ethyl group).

While the optionally substituted aryl group having 6 to 20 carbon atoms is not particularly limited, examples thereof include a phenyl group, a 4-methylphenyl group, a 4-methoxyphenyl group, a 4-nitrophenyl group, and a 4-chlorophenyl group. While the optionally substituted heteroaryl group having 4 to 20 carbon atoms is not particularly limited, examples thereof include a 2-furanyl group, a 2-thiophenyl group, a 2-pyridyl group, and a 4-methyl-2-pyridyl group.

A preferable aryl group is an optionally substituted phenyl group.

In the present invention, of the above-mentioned substituents, a linear, branched, or cyclic alkyl group having 1 to 6 carbon atoms or an aryl group having 6 to 10 carbon atoms is preferred as $R^3$; an ethyl group, an isopropyl group, a n-butyl group, an isobutyl group, a tert-butyl group, a cyclopentyl group, or a phenyl group is more preferred, an ethyl group, an isopropyl group, an isobutyl group, a cyclopentyl group, or a phenyl group is even more preferred, and an isobutyl group, a cyclopentyl group, or a phenyl group is particularly preferred in terms of having excellent absorbability.

In the present invention, any one of $R^1$ and $R^2$ of the compound (1) may be an alkoxycarbonyl group represented by formula (2) or alternatively both of them may be alkoxycarbonyl groups represented by formula (2). When both $R^1$ and $R^2$ are the alkoxycarbonyl groups represented by formula (2), while the alkoxycarbonyl groups may be either different from each other or the same, they are preferably the same in terms of being easy to produce.

The above-described reduced coenzyme $Q_{10}$ derivative of the present invention exhibits excellent oral absorbability though its water solubility is lowered due to substitution of a hydroxyl group, which is a hydrophilic substituent, with a hydrophobic alkoxycarbonyl group. As shown in Examples described infra, carbonated reduced coenzyme $Q_{10}$ derivatives of the present invention such as bisisobutyl carbonate derivatives have oral absorbability higher than that of reduced coenzyme $Q_{10}$. The reduced coenzyme $Q_{10}$ derivative of the present invention (carbonate), which has high oral absorbability though its solubility in water is lower than that of reduced coenzyme $Q_{10}$, is not only novel but also can be said to be a unique compound.

Moreover, since the reduced coenzyme $Q_{10}$ derivative of the present invention can be dissolved in a vegetable oil or the like in a high concentration because of its high lipophilicity, it can be used suitably for soft capsules having a high content, etc.

In addition, the reduced coenzyme $Q_{10}$ derivative of the present invention can also be obtained in the form of crystals. Accordingly, a crystal of the reduced coenzyme $Q_{10}$ derivative represented by the formula (1) is another embodiment of the present invention.

In the crystal of the reduced coenzyme $Q_{10}$ derivative of the present invention, the definitions of $R^1$, $R^2$, and $R^3$ in the formula (1) and the formula (2) are the same as those described supra. In addition, in the crystal of the reduced coenzyme $Q_{10}$ derivative of the present invention, $R^3$ is preferably a linear, branched, or cyclic alkyl group having 2 to 6 carbon atoms or an aryl group having 6 to 10 carbon atoms, $R^3$ is more preferably an ethyl group, an isopropyl group, an isobutyl group, a cyclopentyl group, or a phenyl group, and particularly preferably an isobutyl group, a cyclopentyl group, or a phenyl group. Although $R^1$ and $R^2$ may be either the same or different, they are preferably the same.

In the case of a crystal of a reduced coenzyme $Q_{10}$ derivative wherein $R^1$ and $R^2$ in the formulae (1) and (2) are the same and $R^3$ is an ethyl group, preferred is a crystal of a reduced coenzyme $Q_{10}$ derivative that exhibits diffraction intensity peaks at diffraction angles of 3.48°, 10.70°, 12.48°, 17.94°, 18.60°, 19.44°, and 22.78° in a powder X diffraction pattern.

In addition, in the case of a crystal of a reduced coenzyme $Q_{10}$ derivative wherein $R^1$ and $R^2$ in the formulae (1) and (2) are the same and $R^3$ is an isopropyl group, preferred is a crystal of a reduced coenzyme $Q_{10}$ derivative that exhibits diffraction intensity peaks at diffraction angles of 9.64°, 17.12°, 17.26°, 17.86°, 18.42°, 18.84°, 19.14°, 19.22°, 19.42°, 21.50°, 21.62°, 21.88°, and 23.30° in a powder X diffraction pattern.

In addition, in the case of a crystal of a novel reduced coenzyme $Q_{10}$ derivative wherein $R^1$ and $R^2$ in the formulae (1) and (2) are the same and $R^3$ is an isobutyl group, preferred is a crystal of a reduced coenzyme $Q_{10}$ derivative that exhibits diffraction intensity peaks at diffraction angles of 9.50°, 17.70°, 18.36°, 18.82°, 19.14°, and 22.90° in a powder X diffraction pattern.

In addition, in the case of a crystal of a reduced coenzyme $Q_{10}$ derivative wherein $R^1$ and $R^2$ in the formulae (1) and (2) are the same and $R^3$ is a cyclopentyl group, preferred is a crystal of a reduced coenzyme $Q_{10}$ derivative that exhibits diffraction intensity peaks at diffraction angles of 9.34°, 17.40°, 18.62°, 18.82°, 19.22°, 20.14°, 21.50°, and 22.86° in a powder X diffraction pattern.

In addition, in the case of a crystal of a reduced coenzyme $Q_{10}$ derivative wherein $R^1$ and $R^2$ in the formulae (1) and (2) are the same and $R^3$ is a phenyl group, preferred is a crystal of a reduced coenzyme $Q_{10}$ derivative that exhibits diffraction intensity peaks at diffraction angles of 3.28°, 6.56°, 8.26°, 10.02°, 16.16°, 16.36°, 17.74°, 19.16°, 22.84°, 26.36°, and 26.72° in a powder X diffraction pattern.

Each of the above-mentioned diffraction angles of the powder X diffraction pattern is a value indicating a main peak defined using a diffraction angle 2θ in powder X-ray diffraction obtained by irradiation with a copper Kα beam (wavelength λ=1.54 angstroms), where the main peak as referred to herein is a peak having a relative intensity of not less than about 20 where the intensity of the largest peak among the peaks of the obtained powder X diffraction pattern is taken as 100.

In this specification, when a crystal is defined with the position of a diffraction peak using a diffraction angle 2θ, the value of the diffraction angle 2θ is not limited to a value indicated as having the peak and a range based thereon and may include a margin of errors as a value of a diffraction angle 2θ in a crystal of the present invention. A range within which such errors are generated can be easily expected by a person skilled in the art from a measurement condition and the like, and such a range of errors is, for example, ±0.2°, preferably ±0.1°.

The reduced coenzyme $Q_{10}$ derivative of the present invention capable of being obtained in a crystalline form can be used suitably for powders, tablets, etc. mainly for oral applications.

Next, a method for producing the reduced coenzyme Q10 derivative of the present invention (henceforth "production method of the present invention") is described. While the method for producing the novel reduced coenzyme $Q_{10}$ derivative of the present invention is not particularly limited, a compound (1) represented by the following formula (1):

[Chemical Formula 5]

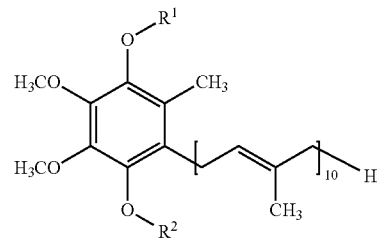

(1)

($R^1$ and $R^2$ are as defined above) can be synthesized by reacting reduced coenzyme $Q_{10}$ represented by the following formula (3):

[Chemical Formula 6]

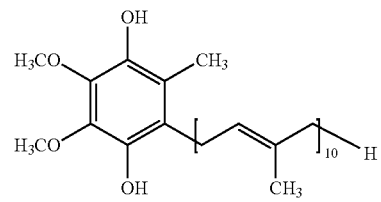

(3)

with an alkoxycarbonylation agent in the presence of a base.

In the production method of the present invention, the reduced coenzyme $Q_{10}$ to be a starting material may be either reduced coenzyme $Q_{10}$ alone or a mixture thereof with oxidized coenzyme $Q_{10}$. When the above-mentioned reduced coenzyme $Q_{10}$ is a mixture thereof with oxidized coenzyme $Q_{10}$, the ratio of the reduced coenzyme $Q_{10}$ in the total amount of coenzyme $Q_{10}$ (i.e., the total amount of reduced coenzyme $Q_{10}$ and oxidized coenzyme $Q_{10}$) is not particularly limited and is, for example, not less than 1 wt %, normally not less than 5 wt %, preferably not less than 10 wt %, more preferably not less than 20 wt %, further preferably not less than 50 wt %, particularly preferably not less than 60 wt %, most preferably not less than 80 wt %.

While the upper limit is not particularly limited, when a mixture with oxidized coenzyme $Q_{10}$ is used as reduced coenzyme $Q_{10}$, it is normally not more than 99.9 wt %. Needless to say, reduced coenzyme $Q_{10}$ may account for 100% by weight of the total amount of coenzyme $Q_{10}$; that is to say, reduced coenzyme $Q_{10}$ may be used alone. The reduced coenzyme $Q_{10}$ to be used here can be obtained by, for example, reducing oxidized coenzyme $Q_{10}$ by a publicly known method, the oxidized coenzyme $Q_{10}$ having been obtained by a conventionally known method, such as synthesis, fermentation, and extraction from a natural product. Preferred is reduced coenzyme $Q_{10}$ obtained from oxidized coenzyme $Q_{10}$ obtained via fermentation or extraction from a natural product. Moreover, as to the reduced coenzyme $Q_{10}$ to be used here, a commercially available product may be used as received or a product prepared by reducing oxidized coenzyme $Q_{10}$ by a publicly known method may be used via isolation and purification. In another possible way, a reaction liquid after a reduction reaction is subjected to such a treatment as washing and concentration if necessary and then used directly as a raw material for the production method of the present invention without performing isolation. In still another possible way, oxidized coenzyme $Q_{10}$ is reduced by a publicly known method and then or at the same time is reacted with an alkoxycarbonylation agent to lead to a compound (1) in one pot.

In the production method of the present invention, the alkoxycarbonylation agent to be used during the reaction is not particularly limited, and examples thereof include a halogenated carbonate represented by the following formula (4):

[Chemical Formula 7]

$$X\text{—}COOR^3 \qquad (4)$$

wherein X represents a halogen atom, $R^3$ is an optionally substituted linear, branched, or cyclic alkyl group having 1 to 20 carbon atoms, an optionally substituted aryl group having 6 to 20 carbon atoms, or an optionally substituted heteroaryl group having 4 to 20 carbon atoms, and when $R^3$ is a group substituted with polyethylene glycol, the molecular weight of the polyethylene glycol is not more than 300, and an acid anhydride represented by the following formula (5):

[Chemical Formula 8]

$$(R^3OCO)_2O \qquad (5)$$

wherein $R^3$ is an optionally substituted linear, branched, or cyclic alkyl group having 1 to 20 carbon atoms, an optionally substituted aryl group having 6 to 20 carbon atoms, or an optionally substituted heteroaryl group having 4 to 20 carbon atoms, and when $R^3$ is a group substituted with polyethylene glycol, the molecular weight of the polyethylene glycol is not more than 300. In the halogenated carbonate of formula (4), while X is not particularly limited as long as it is a halogen atom, preferable is a fluorine atom, a chlorine atom, or a bromine atom, and a chlorine atom is particularly preferable. In the production method of the present invention, the amount of the alkoxycarbonylation agent to be used during the reaction is usually required to be a 1.0-fold molar amount or more based on the compound (3), and while the upper limit is not particularly limited, a 20-fold molar amount or less is large enough from the economical point of view. Preferred is a 1.2- to 15-fold molar amount.

While the solvent to be used during the reaction in the production method of the present invention is not particularly limited, amines, nitriles, amides, hydrocarbons, esters (including fatty acid esters), ethers, ketones, sulfur compounds, and so on may be used. These may be used alone or as a mixed solvent of two or more species thereof.

While the amines used herein are not particularly limited and thus may be cyclic or acyclic and saturated or unsaturated, examples thereof include pyridine, lutidine, N,N-dimethylaniline, triethylamine, diisopropylethylamine, dicyclohexylamine, 1,8-diazabicyclo[5.4.0]undec-7-ene (DBU), and morpholine. Pyridine is preferable.

The above-mentioned nitriles are not particularly limited and they may be either cyclic or acyclic and also may be either saturated or unsaturated. Commonly, however, saturated ones are preferably used. Usually, those having 2 to 20 carbon atoms, particularly those having 2 to 12 carbon atoms, and especially those having 2 to 8 carbon atoms are preferably used. Specific examples thereof include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, nitrobenzonitrile, anisonitrile, phthalonitrile, bromotolunitrile, methylcyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, and tolylcyclohexanecarbonitrile. Preferred are acetonitrile, propionitrile, succinonitrile, butyronitrile, isobutyronitrile, valeronitrile, methyl cyanoacetate, ethyl cyanoacetate, benzonitrile, tolunitrile or chloropropionitrile; more preferred are acetonitrile, propionitrile, butyronitrile and isobutyronitrile; and most preferred is acetonitrile.

Examples of the above-mentioned amides include N,N-dimethylformamide, N,N-dimethylacetamide, and N-methylpyrrolidone.

While the above-mentioned hydrocarbons are not particularly limited, examples thereof include aliphatic hydrocarbons, aromatic hydrocarbons, and halogenated hydrocarbons. In particular, aliphatic hydrocarbons and aromatic hydrocarbons are preferable, and especially, aliphatic hydrocarbons are preferable. While the aliphatic hydrocarbons are not particularly limited and they may be either cyclic or acyclic and may be either saturated or unsaturated, acyclic aliphatic hydrocarbons are particularly preferably used. In addition, those having 5 to 20 carbon atoms are usually used, and those having 5 to 12 carbon atoms are preferably used. Specific examples thereof include pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, and dodecane. Of these, saturated aliphatic hydrocarbons having 5 to 8 carbon atoms are preferable, and pentane, 2-methylbutane, cyclopentane, hexane, 2-methylpentane, 2,2-dimethylbutane, 2,3-dimethylbutane, methylcyclopentane, cyclohexane, heptane, 2-methylhexane, 3-methylhexane, 2,3-dimethylpentane, 2,4-dimethylpentane, methylcyclohexane, octane, 2,2,3-trimethylpentane, isooctane, ethylcyclohexane, etc. are particularly preferable.

While the aromatic hydrocarbons are not particularly limited, those usually having 6 to 20 carbon atoms, particularly having 6 to 12 carbon atoms, and especially having 7 to 10 carbon atoms are preferably used. Specific examples thereof include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, and styrene. Preferred are toluene, xylene, o-xylene, m-xylene, p-xylene, ethylbenzene, cumene, mesitylene, tetralin, butylbenzene, p-cymene, cyclohexylbenzene, diethylbenzene, and pentylbenzene; more preferred are toluene, xylene, o-xylene, m-xylene, p-xylene, cumene, and tetralin; and most preferred is cumene.

The halogenated hydrocarbons are not particularly limited and they may be either cyclic or acyclic and may be either saturated or unsaturated. Commonly, however, acyclic ones are preferably used. In usual, chlorinated hydrocarbons and fluorinated hydrocarbons are preferable, and especially, chlorinated hydrocarbons are preferable. Those having 1 to 6 carbon atoms, particularly having 1 to 4 carbon atoms, and especially having 1 to 2 carbon atoms are preferably used. Specific examples thereof include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, and 1,1,1,2-tetrafluoroethane.

Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, and 1,1,1,2-tetrafluoroethane; and more preferred are dichloromethane, chloroform, 1,2-dichloroethylene, trichloroethylene, chlorobenzene, and 1,1,1,2-tetrafluoroethane.

While the above-mentioned esters (including fatty acid esters) are not particularly limited, examples thereof include propionate esters, acetate esters, and formate esters. Particularly, acetate esters and formate esters are preferable, and especially, acetate esters are preferable. Although not particularly limited, alkyl esters or aralkyl esters having 1 to 8 carbon atoms are commonly used as an ester group, alkyl esters having 1 to 6 carbon atoms are preferably used, and alkyl esters having 1 to 4 carbon atoms are more preferably used. Examples of the propionate esters include methyl propionate, ethyl propionate, butyl propionate, and isopentyl propionate.

Examples of the acetate esters include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate, and cyclohexyl acetate; more preferred are methyl acetate, ethyl acetate, propyl acetate, isopropyl acetate, butyl acetate, and isobutyl acetate; and most preferred is ethyl acetate.

Examples of the formate esters include methyl formate, ethyl formate, propyl formate, isopropyl formate, butyl formate, isobutyl formate, sec-butyl formate, and pentyl formate. Preferred are methyl formate, ethyl formate, propyl formate, butyl formate, isobutyl formate, pentyl formate, etc.; and most preferred is ethyl formate.

While the above-mentioned ethers are not particularly limited and they may be either cyclic or acyclic and may be either saturated or unsaturated, saturated ones are particularly preferably used. Usually, those having 3 to 20 carbon atoms, particularly those having 4 to 12 carbon atoms, and especially those having 4 to 8 carbon atoms are preferably used. Specific examples thereof include diethyl ether, methyl tert-butyl ether, methyl n-butyl ether, dipropyl ether, diisopropyl ether, dibutyl ether, dihexyl ether, ethyl vinyl ether, butyl vinyl ether, anisole, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol dibutyl ether. Preferred are diethyl ether, methyl tert-butyl ether, dipropyl ether, diisopropyl ether, dibutyl ether, dihexyl ether, anisole, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, etc.; more preferred are diethyl ether, methyl tert-butyl ether, anisole, dioxane, tetrahydrofuran, ethylene glycol monomethyl ether, and ethylene glycol monoethyl ether; even more preferred are diethyl ether, methyl tert-butyl ether, and anisole; and most preferred is methyl tert-butyl ether.

The above-mentioned ketones are not particularly limited, and usually, those having 3 to 6 carbon atoms are preferably used. Specific examples thereof include acetone, methyl ethyl ketone, methyl butyl ketone, and methyl isobutyl ketone; preferred are acetone and methyl ethyl ketone; and most preferred is acetone.

Examples of the sulfur compounds include dimethyl sulfoxide and sulfolane.

In the production method of the present invention, the solvent to be used during the reaction is used usually within a range of not less than 1-fold volume amount but not more than 100-fold volume amount based on the weight of the compound (3). Preferred is within a range of not less than 2-fold volume amount but not more than 50-fold volume amount. A 1-fold volume amount to 1 kg of the compound (3) is 1 L.

In the production method of the present invention, a base is used during the reaction. While the base to be used in the production method of the present invention is not particularly limited, a base that is used in a reaction of forming an ester from an alcohol and an acylating agent can be generally used and, for example, organic amines, alkali metal alkoxides, alkali metal hydrides, etc. can be preferably used. Specifically, examples of the organic amines include pyridine, lutidine, N,N-dimethylaniline, triethylamine, diisopropylethylamine, dicyclohexylamine, 1,8-diazabicyclo[5.4.0]undec-7-ene (DBU), and morpholine; examples of the alkali metal alkoxides include potassium tert-butoxide and sodium tert-butoxide; examples of the alkali metal hydrides include sodium hydride and potassium hydride. The use amount of such a base is required to be a 1.0-fold molar amount or more based on the compound (3), and usually, the base is used in a 20-fold molar amount or less. Preferred is a 1.2- to 15-fold molar amount. In the case of an organic amine, it can be used also as a solvent. The use amount of an organic amine in the case where it is used as a base and a solvent is usually within a range of not less than 1-fold volume amount but not more than 100-fold volume amount based on the weight of the compound (3). Preferred is within a range of not less than 2-fold volume amount but not more than 50-fold volume amount.

In the production method of the present invention, while the reaction of synthesizing the compound (1) is performed usually within a range of from −50° C. to the boiling point of the solvent to be used, it is preferably performed at −20 to 40° C. for the reason of inhibiting decomposition of raw materials, intermediates, and products. While the reaction time is usually 1 to 100 hours, it is preferably 2 to 50 hours for the above-mentioned reason. Of course, the reaction time may be adjusted by checking change with time of the reaction by analytic means, such as thin layer chromatography (TLC) and high-performance liquid chromatography (HPLC).

In the production method of the present invention, the target compound (1) can be isolated from the mixture after the reaction usually by using a publicly known post treating method often used in an organic reaction, for example, such operation as pH adjustment, extraction, liquid separation, washing, concentration, and purification.

The compound (1) also can be produced without using the reduced coenzyme $Q_{10}$ of formula (3) as a raw material, not via the above-described production method of the present invention. While the method is not particularly limited, examples thereof include a method in which an alkoxycarbonyl group represented by formula (2) is previously introduced to a hydroquinone skeleton first and then an isoprenoid chain is synthesized according to the method described in JP-A-48-85546 or JP-B-62-31700 and a method using transition from p-position to m-position as described in JP-A-56-123927.

Moreover, to obtain the aforementioned compound (1) in the form of crystals is also one preferable embodiment of the production method of the present invention. In the production method of the present invention, the compound (1) in the form of crystals can be obtained, for example, by treating the compound (1) in a suitable organic solvent. The form of the compound (1) to be used in the crystallization step is not particularly limited and it may be either in a liquid form such as a molten liquid and a solution or in a solid form. Specifically, the compound (1) can be crystallized by dissolving the compound (1) in such a form in an organic solvent according to need and then subjecting the solution to cooling, concentration, poor solvent addition treatment, or the like. When dissolving the compound (1) in an organic solvent, heating may be performed within a range up to the boiling point of the organic solvent to be used. In the production method of the present invention, as the above-mentioned organic solvent to be used in the crystallization step, nitrile, alcohol, aliphatic hydrocarbon, aromatic hydrocarbon, halogenated hydrocarbon, ether, ester, and so on can be used alone, in mixture, or in combination. Specific examples of such nitrile, alcohol, aliphatic hydrocarbon, aromatic hydrocarbon, halogenated hydrocarbon, ether, and ester, and so on are the same as those provided as examples of the solvent capable of being used during the above-described reaction. Of such organic solvents, it is preferable to use nitrile such as acetonitrile and propionitrile; alcohol such as methanol, ethanol, n-propanol, and isopropanol; aliphatic hydrocarbon such as hexane, heptane, and octane; aromatic hydrocarbon such as benzene, toluene, and chlorobenzene; halogenated hydrocarbon such as dichloromethane; ether such as tetrahydrofuran; ester such as ethyl acetate, and so on. They may be used alone, in mixture, or in combination. When the crystallization is performed by cooling and/or concentration, the organic solvent to be used is particularly preferably a nitrile or an alcohol, and the most preferred is acetonitrile or ethanol. The use amount of such particularly preferable organic solvents is not less than 50% by weight, preferably not less than 80% by weight, especially 100% by weight, of the entire solvent. While the amount of the organic solvent to be used for the crystallization may be appropriately determined on the basis of the solubility of the compound (1) in the organic solvent to be used, it is usually 1 to 200-fold weight, preferably 5 to 150-fold weight relative to the compound (1). When cooling is performed during the crystallization, the cooling is usually performed within a range of −80 to 10° C. The crystallization may be performed either in a standing state or in a stirring state. The crystallization may be promoted by adding a seed crystal. The crystallized compound (1) may be isolated as a crystal by a common solid-liquid separation method.

The reduced coenzyme $Q_{10}$ derivative of the present invention may be formulated into a preparation if necessary. The dosage form of the preparation is not particularly limited and it may be either an oral preparation or a preparation applied directly to the skin. The oral preparation may be a powder preparation or may be formed into a granular preparation by adding a binder. In addition, such powder or granules may be packed into capsules to prepare a capsule preparation. The reduced coenzyme $Q_{10}$ derivative of the present invention may be mixed with an excipient of the like according to need and then formed into a tablet.

The reduced coenzyme $Q_{10}$ derivative of the present invention may also be fabricated into soft capsule preparations by adding natural oil, higher fatty acid oil, a higher fatty acid monoglyceride, a higher fatty acid diglyceride, medium chain fatty acid triglyceride (MCT), a surfactant, or a mixture thereof, etc. and filling that in its oily state into capsules. In this case, there also may be used gelatin-based capsules or capsules based on water-soluble polymer substances other than gelatin. Microcapsules are included in such capsules. Alternatively, the derivative may be formed into liquid to prepare a drinkable preparation.

Other carriers (preparation ingredients) may, according to need, be added and mixed with the reduced coenzyme $Q_{10}$ derivative of the present invention by a conventional method. Such materials are not particularly limited and examples thereof include an excipient, a disintegrant, a lubricant, a binder, an antioxidant, a colorant, an anticoagulant, an absorption promoter, a solubilizing agent, and a stabilizer.

The above-mentioned excipient is not particularly limited and examples thereof include sucrose, lactose, glucose, cornstarch, mannitol, crystalline cellulose, calcium phosphate, and calcium sulfate. The above-mentioned disintegrant is not particularly limited and examples thereof include starch, agar, calcium citrate, calcium carbonate, sodium bicarbonate, dextrin, crystalline cellulose, carboxymethylcellulose, tragacanth, and alginic acid.

The above-mentioned lubricant is not particularly limited and examples thereof include talc, magnesium stearate, polyethylene glycol, silica, and hydrogenated vegetable oil. The above-mentioned binder is not particularly limited and examples thereof include ethylcellulose, methylcellulose, hydroxypropylmethylcellulose, tragacanth, shellac, gelatin, pullulan, gum arabic, polyvinylpyrrolidone, polyvinyl alcohol, polyacrylic acid, polymethacrylic acid, and sorbitol.

The above-mentioned antioxidant is not particularly limited and examples thereof include ascorbic acid, tocopherol, vitamin A, β-carotene, sodium bisulfite, sodium thiosulfate, sodium metabisulfite, and citric acid.

The above-mentioned colorant is not particularly limited and examples thereof include those permitted for addition to pharmaceutical products.

The above-mentioned anticoagulant is not particularly limited and examples thereof include stearic acid, talc, light anhydrous silicic acid, and hydrous silicon dioxide.

The above-mentioned absorption promoter is not particularly limited and examples thereof include surfactant such as higher alcohol, higher fatty acid, glycerin ester of fatty acid, sucrose ester of fatty acid, sorbitan ester of fatty acid, polyoxyethylene, sorbitan ester of fatty acid, and polyglycerin ester of fatty acid.

The above-mentioned solubilizing agent is not particularly limited and examples thereof include organic acids such as fumaric acid, succinic acid, and malic acid. The above-mentioned stabilizer is not particularly limited and examples thereof include benzoic acid, sodium benzoate, ethyl p-hydroxybenzoate, beeswax, hydroxypropylmethylcellulose, and methylcellulose.

When applying directly to the skin, the dosage form is not particularly limited, and examples of dosage form include those prepared by dissolving, or mixing and dispersing the above-mentioned drug in a suitable base, into cream, paste, jelly, gel, emulsion or liquid (ointment, liniment, lotion, cream, spray, etc.); those obtained by dissolving, or mixing and dispersing the above-mentioned drug in a base and spreading the resultant on a support (poultices, etc.); and those obtained by dissolving, or mixing and dispersing the above-mentioned drug in an adhesive and spreading the resultant on a support (plaster, tape, etc.). As the base and adhesive, those usually used for medicines and cosmetics may be used according to need as long as the effect of the present invention is not impaired.

The reduced coenzyme $Q_{10}$ derivative of the present invention is allowed, according to need, to exist together with, for example, a surfactant, a colorant, perfume, and an active ingredient other than reduced coenzyme $Q_{10}$ derivatives without any particular limitations.

While the above-mentioned surfactant is not particularly limited, examples thereof include glycerin ester of fatty acid, sucrose ester of fatty acid, organic acid monoglyceride, sorbitan ester of fatty acid, polyoxyethylene sorbitan ester of fatty acid, propylene glycol ester of fatty acid, condensed ricinoleic acid glyceride, saponin, and phospholipid.

While the glycerin ester of fatty acid is not particularly limited, examples thereof include glycerin esters of fatty acids in which the degree of polymerization of glycerin is 1 to 10 and the number of carbon atoms of fatty acids is individually 6 to 18. While the fatty acid residue constituting the glycerol fatty acid ester is not particularly limited, a fatty acid having 6 to 18 carbon atoms may be preferably used and examples thereof include caprylic acid, capric acid, lauric acid, myristic acid, palmitic acid, stearic acid, isostearic acid, oleic acid, linoleic acid, and linolenic acid.

While the sucrose ester of fatty acid is not particularly limited, examples thereof include ones in which fatty acids individually having 6 to 22 carbon atoms are ester-bound to at least one hydroxyl group of sucrose, and specifically include sucrose laurate, sucrose myristate, sucrose palmitate, sucrose stearate, sucrose oleate, sucrose behenate, and sucrose erucate.

While the sorbitan ester of fatty acid is not particularly limited, examples thereof include ones in which fatty acids individually having 6 to 18 carbon atoms are ester-bound to at least one hydroxyl group of sorbitan, and specifically include sorbitan monolaurate, sorbitan monopalmitate, sorbitan monostearate, and sorbitan monooleate.

While the polyoxyethylene sorbitan ester of fatty acid is not particularly limited, examples thereof include polyoxyethylene sorbitan monopalmitate, polyoxyethylene sorbitan monostearate, polyoxyethylene sorbitan monooleate, polyoxyethylene sorbitan tristearate, and polyoxyethylene sorbitan trioleate, to each of which 6- to 20-mols of ethylene oxide chain is added.

While the condensed ricinoleic acid glyceride is not particularly limited, examples thereof include polyglycerin condensed ricinoleate for which the average degree of polyglycerin polymerization is 2 to 10 and the average degree of polyricinoleic acid condensation (the average number of condensed ricinoleic acids) is 2 to 4, and specifically include tetraglycerin condensed ricinoleate, pentaglycerin condensed ricinoleate, and hexaglycerin condensed ricinoleate.

As the propylene glycol fatty acid ester, either propylene glycol fatty acid monoester or propylene glycol fatty acid diester may be used. While the fatty acid residue constituting the propylene glycol ester of fatty acid is not particularly limited, a fatty acid having 6 to 18 carbon atoms may be preferably used and specific examples thereof include caprylic acid, capric acid, lauric acid, myristic acid, palmitic acid, stearic acid, isostearic acid, oleic acid, linoleic acid, and linolenic acid.

While the phospholipid is not particularly limited, examples thereof include egg yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphorylglycerol, and mixtures thereof. Needless to say, phospholipids processed via hydrogenation, enzymatic degradation, or the like also may be used. In view of the improvement in absorbability of a reduced coenzyme $Q_{10}$ derivative, it is preferable to use an enzymatically degraded phospholipid.

While the saponin is not particularly limited, examples thereof include enju saponin, quillaja saponin, purified soybean saponin, and yucca saponin.

While the above-mentioned dye is not particularly limited, examples thereof include titanium oxide, synthetic dyes, colcothar dye, and tar dye.

While the above-mentioned perfume is not particularly limited, examples thereof include orange oil, capsicum oil, mustard oil, garlic oil, callaway oil, clove oil, cinnamon oil, cocoa extract, coffee bean extract, ginger oil, spearmint oil, celery-seed oil, thyme oil, onion oil, nutmeg oil, parsley seed oil, mint oil, vanilla extract, fennel oil, pennyroyal oil, peppermint oil, eucalyptus oil, lemon oil, rose oil, rosemary oil, almond oil, ajowan oil, anise oil, amyris oil, angelica root oil, ambrette seed oil, estragon oil, origanum oil, orris root oil, olibanum oil, cassia oil, cascarilla oil, cananga oil, chamomile oil, calamus oil, cardamom oil, carrot seed oil, cubeb oil, cumin oil, grapefruit oil, cinnamon leaf oil, cade oil, pepper oil, costus root oil, congnac oil, cop aiba oil, cilantro oil, perilla oil, musk, juniper berry oil, star anis oil, sage oil, savory oil, geranium oil, tangerin oil, dill oil, neroli oil, tolu balsam oil, basil oil, birch oil, patchouli oil, palmarosa oil, pimento oil, petitgrain oil, bay leaf oil, bergamot oil, peru balsam oil, benzoin resin, Bois de Rose oil, hop oil, boronia absolute, marjoram oil, mandarin oil, myrtle oil, Chinese lemon flavor, lime oil, lavandin oil, lavender oil, rue oil, lemongrass oil, lenthionine, lavage oil, laurel leaf oil, and worm wood oil.

The above-mentioned substances may have two or more roles. For example, starch may have roles of an excipient and a disintegrant.

Pharmaceutical preparations containing the reduced coenzyme $Q_{10}$ derivative of the present invention may also contain other nutritional fortification components. While the nutritional fortification components are not particularly limited, for example, creatine, taurine, vitamin B1, vitamin B derivatives, amino acids, etc. are suitable. These may be used either singly or in a combination of two or more thereof. By mixing the reduced coenzyme $Q_{10}$ derivative of the present invention with such ingredients, further additive or synergistic effects can be expected.

Pharmaceutical preparations containing the reduced coenzyme $Q_{10}$ derivative of the present invention may also contain a nutritious supplement component. While the a nutritious supplement component is not particularly limited, examples thereof include amino acids, metal ions, saccharides, proteins, fatty acids, and vitamins.

When the reduced coenzyme $Q_{10}$ derivative of the present invention is made to be contained in a general food, the form of the food is not particularly limited and examples thereof include edible fat and oil composition, cooking oil, spray oil, butter, margarine, shortening, whipping cream, concentrated milk, whiteners, dressings, pickle liquids, breads, cakes, pies, cookies, Japanese confectionaries, snacks, fried snacks, chocolates and chocolate confectionaries, rice confectionaries, roux, sauce, basting, toppings, ice creams, noodles, bread mix, fried food, processed meat products, fish paste products, frozen food such as frozen entrees, frozen meat and frozen vegetables, rice, jam, cheese, cheese food, cheese-like food, chewing gums, candies, fermented milk, canned food, and drinks.

The present application claims the benefit of priority to Japanese Patent Application Number 2012-264558 filed on Dec. 3, 2012. The entire contents of the specification of Japanese Patent Application Number 2012-264558 filed on Dec. 3, 2012 are hereby incorporated in its entirety as a reference for the present application.

EXAMPLES

The present invention is hereafter described in greater detail with reference to the following examples, but the present invention is not limited thereto.
(NMR Measurement Conditions)
Apparatus: JEOL 400 MHz Rhamda or JEOL 500 MHz ECA-500 Delta
(Powder X-Ray Diffraction (XRD) Measurement Conditions)
Apparatus: MiniFlexII manufactured by Rigaku Corporation
X-ray used: Cu—Kα beam
Strength: 30 kV, 15 mA
Angle: 2θ=2 to 60°
Scattering speed: 2°/min
Divergence slit (DS): 1.25°
Scatter slit (SS): 1.25°
Receiving slit (RS): 0.3 mm Example 1

Reduced Coenzyme $Q_{10}$ with the Hydroxyl Groups at its 1- and 4-Positions Having been Ethoxycarbonylated (Bisethyl Carbonate Derivative)

Ten grams of reduced coenzyme $Q_{10}$ crystals were weighed in a flask, followed by flashing with nitrogen. Then, 50 ml of pyridine was added and the crystals were dissolved therein, followed by flashing with nitrogen again. Subsequently, ethyl chloroformate was dropped at room temperature and addition of ethyl chloroformate was continued until unreacted reduced coenzyme $Q_{10}$ and a reaction intermediate disappeared while checking the advance of the reaction by TLC. As a result, the amount of the ethyl chloroformate added was 12 ml. The reaction liquid was diluted by addition of 100 ml of hexane and then pyridine hydrochloride precipitated was removed by filtration. To the resulting filtrate was added 100 ml of purified water and then the layers were allowed to separate, so that the desired product was extracted to the organic layer. The separated aqueous layer was re-extracted with 100 ml of hexane. The combined organic layers were washed with 100 ml of purified water, dried over sodium sulfate, and then dried, filtered, concentrated, and vacuum dried, so that a crude product of a bisethyl carbonate derivative was obtained. The resulting crude product of the bisethyl carbonate derivative was dissolved in 100 ml of ethyl acetate and the insoluble material was removed by filtration. The filtrate was concentrated and the concentrate was dissolved at 50° C. by addition of 1000 ml of ethanol. Subsequently, the solution was cooled slowly to 4° C., so that crystals were formed. The resulting milk white solid was collected by filtration and vacuum dried, so that a bisethyl carbonate derivative (7.9 g) in the form of crystals was obtained.

Melting point: 39° C.
$^1$H-NMR(CDCl$_3$) δ: 5.04-5.14 (m, 9H); 5.00 (t, J=6.2 Hz, 1H); 4.33 (q, J=7.1 Hz, 2H); 4.21 (q, J=7.2 Hz, 2H); 3.87 (s+s; 6H); 3.27 (d, J=6.3 Hz, 2H); 1.93-2.13 (m, 36H); 1.73 (s, 3H); 1.68 (s, 3H); 1.56-1.64 (m, 27H); 1.55 (s, 3H); 1.40 (t, J=7.1 Hz, 3H); 1.38 (t, J=7.1 Hz, 3H)

In addition, powder X-ray diffraction analysis of the resulting crystals was performed. Results are shown in Table 1.

TABLE 1

Powder X-ray diffraction spectrum data of bisethyl carbonate derivative

| Diffraction angle (°) | Relative intensity |
| --- | --- |
| 3.480 | 25 |
| 10.700 | 23 |
| 12.480 | 20 |
| 17.940 | 21 |
| 18.600 | 100 |
| 19.440 | 22 |
| 22.780 | 56 |

Example 2

Reduced Coenzyme $Q_{10}$ with the Hydroxyl Groups at its 1- and 4-Positions Having been Isopropyloxycarbonylated (Bisisopropyl Carbonate Derivative)

Two grams of reduced coenzyme $Q_{10}$ crystals were weighed in a flask, followed by flashing with nitrogen. Then, 20 ml of pyridine was added and the crystals were dissolved therein, followed by flashing with nitrogen again. Subsequently, isopropyl chloroformate was dropped at room temperature and addition of isopropyl chloroformate was continued until unreacted reduced coenzyme $Q_{10}$ and a reaction intermediate disappeared while checking the advance of the reaction by TLC. As a result, the amount of the isopropyl chloroformate added was 1.1 ml. The reaction liquid was diluted by addition of 50 ml of hexane and then pyridine hydrochloride precipitated was removed by filtration. To the resulting filtrate was added 40 ml of purified water and then the layers were allowed to separate, so that the desired product was extracted to the organic layer. The separated aqueous layer was re-extracted twice with 40 ml of hexane. The combined organic layers were washed with 40 ml of purified water, dried over sodium sulfate, and then dried, filtered, concentrated, and vacuum dried, so that a crude product of a bisisopropyl carbonate derivative was obtained. The resulting crude product of the bisisopropyl carbonate derivative was dissolved at 50° C. by addition of 100 ml of ethanol. Subsequently, the solution was cooled slowly to −15° C., so that crystals were formed. The resulting slight yellow solid was collected by filtration and vacuum dried, so that a bisisopropyl carbonate derivative (1.9 g) in the form of crystals was obtained.

Melting point: 40° C.

$^1$H-NMR(CDCl$_3$) δ: 5.05-5.14 (m, 9H); 4.93-5.03 (t, 3H); 3.87 (s, 6H); 3.27 (d, J=6.3 Hz, 2H); 2.10 (s, 3H); 1.93-2.10 (m, 36H); 1.73 (s, 3H); 1.68 (s, 3H); 1.54-1.62 (m, 27H); 1.39 (d, J=6.3 Hz, 6H); 1.37 (d, J=6.3 Hz, 6H)

In addition, powder X-ray diffraction analysis of the resulting crystals was performed. Results are shown in Table 2.

TABLE 2

Powder X-ray diffraction spectrum data of bisisopropyl carbonate derivative

| Diffraction angle (°) | Relative intensity |
| --- | --- |
| 9.640 | 32 |
| 17.120 | 31 |
| 17.260 | 21 |
| 17.860 | 20 |
| 18.420 | 100 |
| 18.840 | 52 |
| 19.140 | 42 |
| 19.220 | 53 |
| 19.420 | 24 |
| 21.500 | 24 |
| 21.620 | 30 |
| 21.880 | 65 |
| 23.300 | 45 |

Example 3

Reduced Coenzyme Q$_{10}$ with the Hydroxyl Groups at its 1- and 4-Positions Having been Isobutyloxycarbonylated (Bisisobutyl Carbonate Derivative)

Two grams of reduced coenzyme Q$_{10}$ crystals were weighed in a flask, followed by flashing with nitrogen. Then, 20 ml of pyridine was added and the crystals were dissolved therein, followed by flashing with nitrogen again. Subsequently, isobutyl chloroformate was dropped at room temperature and addition of isobutyl chloroformate was continued until unreacted reduced coenzyme Q$_{10}$ and a reaction intermediate disappeared while checking the advance of the reaction by TLC. As a result, the amount of the isobutyl chloroformate added was 0.74 ml. The reaction liquid was diluted by addition of 50 ml of hexane and then pyridine hydrochloride precipitated was removed by filtration. To the resulting filtrate was added 40 ml of purified water and then the layers were allowed to separate, so that the desired product was extracted to the organic layer. The separated aqueous layer was re-extracted twice with 40 ml of hexane. The combined organic layers were washed with 40 ml of purified water, dried over sodium sulfate, and then dried, filtered, concentrated, and vacuum dried, so that a crude product of a bisisobutyl carbonate derivative was obtained. The resulting crude product of the bisisobutyl carbonate derivative was dissolved at 50° C. by addition of 100 ml of ethanol. Subsequently, the solution was cooled slowly to −15° C., so that crystals were formed. The resulting slight yellow solid was collected by filtration and vacuum dried, so that a bisisobutyl carbonate derivative (2.1 g) in the form of crystals was obtained.

Melting point: 35° C.

$^1$H-NMR(CDCl$_3$) δ: 5.05-5.14 (m, 9H); 5.00 (t, J=6.4 Hz, 1H); 4.06 (d, J=6.9 Hz, 2H); 4.04 (d, J=6.9 Hz, 2H); 3.86 (s, 6H); 3.27 (d, J=6.3 Hz, 2H); 2.11 (s, 3H); 1.93-2.10 (m, 36H); 1.73 (s, 3H); 1.68 (s, 3H); 1.54-1.63 (m, 29H); 1.00 (d, J=6.9 Hz, 6H); 0.99 (d, J=6.9 Hz, 6H)

In addition, powder X-ray diffraction analysis of the resulting crystals was performed. Results are shown in Table 3.

TABLE 3

Powder X-ray diffraction spectrum data of bisisobutyl carbonate derivative

| Diffraction angle (°) | Relative intensity |
| --- | --- |
| 9.500 | 21 |
| 17.700 | 27 |
| 18.360 | 26 |
| 18.820 | 100 |
| 19.140 | 43 |
| 22.900 | 27 |

Example 4

Reduced Coenzyme Q$_{10}$ with the Hydroxyl Groups at its 1- and 4-Positions Having been Cyclopentyloxycarbonylated (Biscyclopentyl Carbonate Derivative)

One gram of reduced coenzyme Q$_{10}$ crystals were weighed in a flask, followed by flashing with nitrogen. Then, 10 ml of pyridine was added and the crystals were dissolved therein, followed by flashing with nitrogen again. Subsequently, cyclopentyl chloroformate was dropped at room temperature and addition of cyclopentyl chloroformate was continued until unreacted reduced coenzyme Q$_{10}$ and a reaction intermediate disappeared while checking the advance of the reaction by TLC. As a result, the amount of the cyclopentyl chloroformate added was 0.8 ml. The reaction liquid was diluted by addition of 50 ml of hexane and then pyridine hydrochloride precipitated was removed by filtration. To the resulting filtrate was added 40 ml of purified water and then the layers were allowed to separate, so that the desired product was extracted to the organic layer. The separated aqueous layer was re-extracted twice with 40 ml of hexane. The combined organic layers were washed with 40 ml of purified water, dried over sodium sulfate, and then dried, filtered, concentrated, and vacuum dried, so that a crude product of a biscyclopentyl carbonate derivative was obtained. The resulting crude product of the biscyclopentyl carbonate derivative was dissolved at 50° C. by addition of 100 ml of ethanol. Subsequently, the solution was cooled slowly to −15° C., so that crystals were formed. The resulting slight yellow solid was collected by filtration and vacuum dried, so that a biscyclopentyl carbonate derivative (1.1 g) in the form of crystals was obtained.

Melting point: 41° C.

$^1$H-NMR(CDCl$_3$) δ: 5.19 (m, 2H); 5.06-5.14 (m, 9H); 4.99 (t, J=6.0 Hz, 1H); 3.86 (s, 6H); 3.26 (d, J=6.3 Hz, 2H); 1.75-2.10 (m, 47H); 1.73 (s, 3H); 1.68 (s, 3H); 1.54-1.67 (m, 35H)

In addition, powder X-ray diffraction analysis of the resulting crystals was performed. Results are shown in Table 4.

TABLE 4

Powder X-ray diffraction spectrum data of biscyclopentyl carbonate derivative

| Diffraction angle (°) | Relative intensity |
|---|---|
| 9.340 | 22 |
| 17.400 | 37 |
| 18.620 | 100 |
| 18.820 | 87 |
| 19.220 | 41 |
| 20.140 | 25 |
| 21.500 | 27 |
| 22.860 | 47 |

Example 5

Reduced Coenzyme Q$_{10}$ with the Hydroxyl Groups at its 1- and 4-Positions Having been Phenyloxycarbonylated (Bisphenyl Carbonate Derivative)

Two grams of reduced coenzyme Q$_{10}$ crystals were weighed in a flask, followed by flashing with nitrogen. Then, 20 ml of pyridine was added and the crystals were dissolved therein, followed by flashing with nitrogen again. Subsequently, phenyl chloroformate was dropped at room temperature and addition of phenyl chloroformate was continued until unreacted reduced coenzyme Q$_{10}$ and a reaction intermediate disappeared while checking the advance of the reaction by TLC. As a result, the amount of the phenyl chloroformate added was 0.8 ml. The reaction liquid was diluted by addition of 40 ml of hexane and then pyridine hydrochloride precipitated was removed by filtration. To the resulting filtrate was added 80 ml of 4% aqueous sodium bicarbonate and then the layers were allowed to separate, so that the desired product was extracted to the organic layer. The separated aqueous layer was re-extracted twice with 40 ml of hexane. The combined organic layers were washed with 40 ml of 4% aqueous sodium bicarbonate, dried over sodium sulfate, and then dried, filtered, concentrated, and vacuum dried, so that a crude product of a bisphenyl carbonate derivative was obtained. The resulting crude product of the bisphenyl carbonate derivative was dissolved at 65° C. by addition of 200 ml of ethanol. Subsequently, the solution was cooled slowly to −15° C., so that crystals were formed. The resulting slight yellow solid was collected by filtration and vacuum dried, so that a bisphenyl carbonate derivative (2.1 g) in the form of crystals was obtained.

Melting point: 52° C.

$^1$H-NMR(CDCl$_3$) δ: 7.38-7.44 (m, 4H); 7.23-7.30 (m, 6H); 5.03-5.14 (m, 10H); 3.94 (s, 6H); 3.38 (d, J=6.3 Hz, 2H); 2.22 (s, 3H); 1.92-2.10 (m, 36H); 1.79 (s, 3H); 1.68 (s, 3H); 1.57-1.61 (m, 24H); 1.56 (s, 3H)

In addition, powder X-ray diffraction analysis of the resulting crystals was performed. Results are shown in Table 5.

TABLE 5

Powder X-ray diffraction spectrum data of bisphenyl carbonate derivative

| Diffraction angle (°) | Relative intensity |
|---|---|
| 3.280 | 26 |
| 6.560 | 63 |
| 8.260 | 63 |
| 10.020 | 35 |
| 16.160 | 21 |
| 16.360 | 25 |
| 17.740 | 65 |
| 19.160 | 94 |
| 22.840 | 100 |
| 26.360 | 20 |
| 26.720 | 41 |

Example 6

Reduced Coenzyme Q$_{10}$ with the Hydroxyl Groups at its 1- and 4-Positions Having been n-Butyloxycarbonylated (Bis-N-Butyl Carbonate Derivative)

Two grams of reduced coenzyme Q$_{10}$ crystals were weighed in a flask, followed by flashing with nitrogen. Then, 20 ml of pyridine was added and the crystals were dissolved therein, followed by flashing with nitrogen again. Subsequently, n-butyl chloroformate was dropped at room temperature and addition of n-butyl chloroformate was continued until unreacted reduced coenzyme Q$_{10}$ and a reaction intermediate disappeared while checking the advance of the reaction by TLC. As a result, the amount of the n-butyl chloroformate added was 0.75 ml. The reaction liquid was diluted by addition of 50 ml of hexane and then pyridine hydrochloride precipitated was removed by filtration. To the resulting filtrate was added 40 ml of purified water and then the layers were allowed to separate, so that the desired product was extracted to the organic layer. The separated aqueous layer was re-extracted twice with 40 ml of hexane. The combined organic layers were washed with 40 ml of purified water, dried over sodium sulfate, and then dried, filtered, concentrated, and vacuum dried, so that a crude product of a bis-n-butyl carbonate derivative was obtained. The crude product of a bis-n-butyl carbonate derivative was purified by silica gel column chromatography (hexane:ethyl acetate=19:1 to 9:1), so that the bis-n-butyl carbonate derivative (1.2 g) was obtained. Although it was in the form of crystals under refrigerated conditions, it became oily at room temperature.

$^1$H-NMR(CDCl$_3$) δ: 5.05-5.15 (m, 9H); 5.01 (t, J=6.2 Hz, 1H); 4.28 (t, J=6.5 Hz, 2H); 4.25 (t, J=6.5 Hz, 2H); 3.86 (s, 6H); 3.27 (d, J=6.2 Hz, 2H); 1.92-2.12 (m, 39H); 1.73 (m, 7H); 1.68 (s, 3H); 1.5 5-1.61 (m, 27H); 1.38-1.49 (m, 4H); 0.93-0.99 (m, 61)

Example 7

Reduced Coenzyme $Q_{10}$ with One of the Hydroxyl Groups at its 1,4-Positions Having been Isobutyloxycarbonylated (Monoisobutyl Carbonate Derivative)

Twenty grams of reduced coenzyme $Q_{10}$ crystals were weighed in a flask, followed by flashing with nitrogen. Then, 200 ml of n-hexane and 20 g of pyridine were added and the crystals were dissolved. Under cooling on ice, isobutyl chloroformate was dropped at room temperature and addition of isobutyl chloroformate was continued until unreacted reduced coenzyme $Q_{10}$ and a reaction intermediate disappeared while checking the advance of a reaction by TLC. As a result, the amount of the isobutyl chloroformate added was 12.8 g. The reaction liquid was added to 200 ml of ice water and then the organic layer was obtained. The organic layer was washed twice with 100 ml of purified water, dried over sodium sulfate, and then dried, filtered, concentrated, and vacuum dried, so that a crude product of a monoisobutyl carbonate derivative was obtained. The crude product of the monoisobutyl carbonate derivative was purified by silica gel column chromatography (hexane:ethyl acetate=20:1), so that a monoisobutyl carbonate derivative with its 1- or 4-position having been isobutyloxycarbonylated was obtained.

$^1$H-NMR(CDCl$_3$) δ: 5.69 (s, 1H); 5.05-5.14 (m, 10H); 4.06 (d, J=6.9 Hz, 2H); 3.92 (s, 3H); 3.85 (s, 3H); 3.34 (d, J=6.9 Hz, 2H); 1.90-2.12 (m, 39H); 1.76 (s, 3H); 1.68 (s, 3H); 1.52-1.63 (m, 28H); 1.00 (d, J=6.9 Hz, 6H)

$^1$H-NMR(CDCl$_3$) δ: 5.72 (s, 1H); 5.05-5.14 (m, 9H); 5.01 (m, 1H); 4.03 (d, J=6.9 Hz, 2H); 3.92 (s, 3H); 3.85 (s, 3H); 3.25 (d, J=6.2 Hz, 2H); 2.15 (s, 3H); 1.90-2.11 (m, 36H); 1.73 (s, 3H); 1.68 (s, 3H); 1.52-1.63 (m, 28H); 0.99 (d, J=6.9 Hz, 6H)

Example 8

A crude product of a bisisopropyl carbonate derivative was obtained by the same method as Example 2. To 1.0 g of the obtained crude product of the bisisopropyl carbonate derivative were added 5 g of ethyl acetate and 45 g of acetonitrile, and the crude product was dissolved at 50° C. and then cooled slowly to 20° C. Then, a seed crystal was added. Moreover, crystallization was promoted by cooling slowly to −10° C. and then aging was carried out at 5° C. The resulting white needle-like crystals were collected by filtration and vacuum dried, so that 650 mg of a bisisopropyl carbonate derivative in the form of crystals was obtained.

The powder X-ray diffraction analysis of the resulting crystals revealed that there was no difference from the results of the powder X-ray diffraction analysis of Example 2 and they were crystals of the same form.

Referential Example 1

Reduced Coenzyme $Q_{10}$ with the Hydroxyl Groups at its 1- and 4-Positions Having been Acetylated (Bisacetyl Derivative)

Ten grams of reduced coenzyme $Q_{10}$ crystals were weighed in a flask, followed by flashing with nitrogen. Then, 50 ml of pyridine was added and the crystals were dissolved therein, followed by flashing with nitrogen again. Subsequently, 3 ml of acetic anhydride was dropped at room temperature. After stirring for 3 hours, the reaction liquid was diluted by addition of 100 ml of hexane, and then the resultant was added to 100 ml of ice water and thereby the reaction was stopped. After separating the organic layer, the aqueous layer separated was re-extracted with 100 ml of hexane. The combined organic layers were washed twice with 100 ml of purified water, dried over sodium sulfate, and then dried, filtered, concentrated, and vacuum dried, so that a crude product of a bisacetyl derivative was obtained. To the obtained crude product of the bisacetyl derivative was added 400 ml of ethanol, and the crude product was dissolved therein at 55° C., followed by cooling slowly. The resulting milk white solid was collected by filtration and vacuum dried, so that the bisacetyl (7.3 g) was obtained.

Melting point: 42 to 44° C.

$^1$H-NMR(CDCl$_3$) δ: 5.04-5.14 (m, 9H); 4.98 (t, J=6.1 Hz, 1H); 3.83 (s+s, 6H); 3.21 (d, J=6.6 Hz, 2H); 2.35 (s, 3H); 2.31 (s, 3H); 1.92-2.10 (m, 39H); 1.73 (s, 3H); 1.68 (s, 3H); 1.52-1.65 (m, 27H)

Example 9

To seven-weeks old male Spregue-Dawley rats (obtained from Japan SLC, Inc.) were orally administered the derivatives of reduced coenzyme $Q_{10}$ obtained in Examples 3, 4 and 5 and the starting reduced coenzyme $Q_{10}$ as control each in 57.8 μmol/kg (50 mg/kg in terms of reduced coenzyme $Q_{10}$). Blood was extracted from each rat after 1, 2, 4, 8 and 24 hours after administration of each sample. Each extracted blood was centrifuged, so that plasma was obtained. Then, oxidation treatment of reduced coenzyme $Q_{10}$ in the plasma and extraction treatment of oxidized coenzyme $Q_{10}$ were performed, and then the overall coenzyme $Q_{10}$ concentration in the plasma was measured as oxidized coenzyme $Q_{10}$ by using HPLC.

As the result, as shown in Table 6 below, it was confirmed that the reduced coenzyme $Q_{10}$ derivatives of the present invention exhibited higher areas under the blood concentration-time curve (hereinafter AUC) and were superior in oral absorbability as compared with reduced coenzyme $Q_{10}$ (in the following table, the AUC of each derivative is expressed by a relative value where the AUC (μg/mL*hr) of the case where reduced coenzyme $Q_{10}$ was made to take was assigned as 100).

TABLE 6

| Compound | AUC relative value |
| --- | --- |
| Reduced coenzyme $Q_{10}$ | 100 |
| Bisisobutyl carbonate derivative | 181 |
| Biscyclopentyl carbonate derivative | 120 |
| Bisphenyl carbonate derivative | 144 |

Comparative Example 1

To seven-weeks old male Spregue-Dawley rats (obtained from Japan SLC, Inc.) were orally administered the derivative of reduced coenzyme $Q_{10}$ obtained in Referential Example 1 and the starting reduced coenzyme $Q_{10}$ as control each in 57.8 μmol/kg (50 mg/kg in terms of reduced coenzyme $Q_{10}$). Blood was extracted from each rat after 1, 2, 4, 8 and 24 hours after administration of each sample. Each extracted blood was centrifuged, so that plasma was obtained. Then, oxidation treatment of reduced coenzyme $Q_{10}$ in the plasma and extraction treatment of oxidized coenzyme $Q_{10}$ were performed, and then the overall coenzyme $Q_{10}$ concentration in the plasma was measured as oxidized coenzyme $Q_{10}$ by using HPLC.

As the result, as shown in Table 7 below, it was confirmed that the AUC of the bisacetyl derivative of Referential Example 1 is lower as compared with reduced coenzyme $Q_{10}$ and oral absorbability is lowered by acetylation (the AUC of the bisacetyl derivative is expressed by a relative value where the AUC of the case where reduced coenzyme $Q_{10}$ was made to take was assigned as 100).

TABLE 7

| Compound | AUC relative value |
| --- | --- |
| Reduced coenzyme $Q_{10}$ | 100 |
| Bisacetyl derivative | 69 |

INDUSTRIAL APPLICABILITY

The reduced coenzyme $Q_{10}$ derivative of the present invention can be used for foods and drinks such as health foods or foods with health claims (foods for specified health use and foods with nutrient function claims), pharmaceutical products, quasi drugs, cosmetics, etc.

The invention claimed is:

1. A reduced coenzyme $Q_{10}$ derivative represented by formula (1),

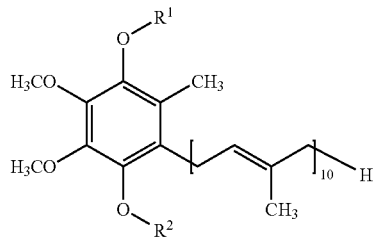

wherein $R^1$ and $R^2$ are each independently H or an alkoxycarbonyl group represented by formula (2),

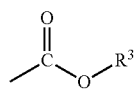

and at least one of $R^1$ and $R^2$ is an alkoxycarhonyl group represented by formula (2), and $R^3$ is a linear, branched, or cyclic alkyl group having 1 to 6 carbon atoms, or an aryl group having 6 to 10 carbon atoms.

2. The reduced coenzyme $Q_{10}$ derivative according to claim 1, wherein $R^1$ and $R^2$ are the same.

3. A crystal of a reduced coenzyme $Q_{10}$ derivative represented by formula (1),

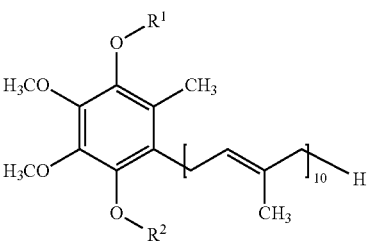

wherein $R^1$ and $R^2$ are each independently H or an alkoxycarbonyl group represented by formula (2),

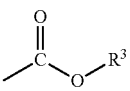

and at least one of $R^1$ and $R^2$ is an alkoxycarbonyl group represented by formula (2), and $R^3$ is a linear, branched, or cyclic alkyl group having 1 to 6 carbon atoms, or an aryl group having 6 to 10 carbon atoms.

4. The crystal of the reduced coenzyme $Q_{10}$ derivative according to claim 3, wherein $R^3$ is an ethyl group, an isopropyl group, an isobutyl group, a cyclopentyl group, or a phenyl group.

5. The crystal of the reduced coenzyme $Q_{10}$ derivative according to claim 3, wherein $R^1$ and $R^2$ are the same.

6. A method for producing the reduced coenzyme $Q_{10}$ derivative according to claim 1, comprising:
reacting reduced coenzyme $Q_{10}$ represented by formula (3):

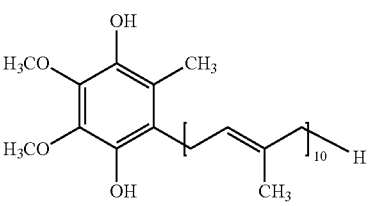

with an alkoxycarbonylation agent in the presence of a base.

7. The method according to claim 6, further comprising:
forming crystals in an organic solvent.

8. The method according to claim 7, wherein the organic solvent comprises one or more organic solvents selected from the group consisting of a nitrile, an alcohol, an aliphatic hydrocarbon, an aromatic hydrocarbon, a halogenated hydrocarbon, an ether, and an ester.

9. The method according to claim 7, wherein the organic solvent is at least one of a nitrile and an alcohol.

10. The method according to claim 8, wherein the organic solvent is a nitrile.

11. The method according to claim 10, wherein the nitrile is acetonitrile.

12. The method according to claim 8, wherein the organic solvent is an alcohol.

13. The method according to claim 12, wherein the alcohol is ethanol.

14. The reduced coenzyme $Q_{10}$ derivative according to claim 1, wherein $R^1$ and $R^2$ are each represented by the formula (2).

15. The crystal of the reduced coenzyme $Q_{10}$ derivative according to claim 3, wherein $R^1$ and $R^2$ are each represented by the formula (2).

16. The crystal of the reduced coenzyme $Q_{10}$ derivative according to claim 4, wherein $R^1$ and $R^2$ are the same.

17. The reduced coenzyme $Q_{10}$ derivative according to claim 1, wherein $R^3$ is an ethyl group, an isopropyl group, a n-butyl group, an isobutyl group, a tert-butyl group, a cyclopentyl group, or a phenyl group.

18. The reduced coenzyme $Q_{10}$ derivative according to claim 1, wherein $R^3$ is an isopropyl group, a cyclopentyl group, or a phenyl group.

19. The reduced coenzyme $Q_{10}$ derivative according to claim 18, wherein $R^1$ and $R^2$ are the same.

20. The crystal of the reduced coenzyme $Q_{10}$ derivative according to claim 3, wherein $R^3$ is a linear, branched, or cyclic alkyl group having 2 to 6 carbon atoms.

* * * * *